United States Patent [19]

Ebata et al.

[11] Patent Number: 5,319,108

[45] Date of Patent: Jun. 7, 1994

[54] METHOD FOR PRODUCING (R,Z)-5-TETRADECEN-4-OLIDE

[75] Inventors: Takashi Ebata; Hiroshi Kawakami; Koshi Koseki; Hajime Matsushita, all of Yokohama; Mikio Ono, Hamura, all of Japan

[73] Assignees: Japan Tobacco Inc.; Fuji Flavor Co., Ltd., Tokyo, Japan

[21] Appl. No.: 782,595

[22] Filed: Oct. 25, 1991

[30] Foreign Application Priority Data

Oct. 26, 1990 [JP] Japan ................................. 2-286953

[51] Int. Cl.$^5$ ............................................. C07D 307/33
[52] U.S. Cl. ................................................... 549/295
[58] Field of Search .......................... 424/84; 549/295

[56] References Cited

PUBLICATIONS

P. A. Levene et al., *Acetone Derivatives of d-Ribose,* J. Biol. Chem., 102, pp. 187–201(1933).
Yoshihiro Nishida et al., "Syntheses of Chiral γ-Lactones from D-and L- Arabinoses", *Agric. Biol. Chem.,* 51(3), 635–640, 1987.
Shuji Senda et al., "Asymmetric Synthesis of (R,Z) . . . ", *Agric. Biol. Chem.,* 47(11), 2595–2598, 1983.
R. E. Doolittle et al., "Synthesis of the Sex Pheromone . . . ", *Plenum Publishing Corporation,* pp. 473–485, 1980.

*Primary Examiner*—C. Warren Ivy
*Assistant Examiner*—A. Owens
*Attorney, Agent, or Firm*—Birch, Stewart, Kolasch & Birch

[57] ABSTRACT

A method for producing (R,Z)-5-tetradecen-4-olide, comprising the following reaction formulas;

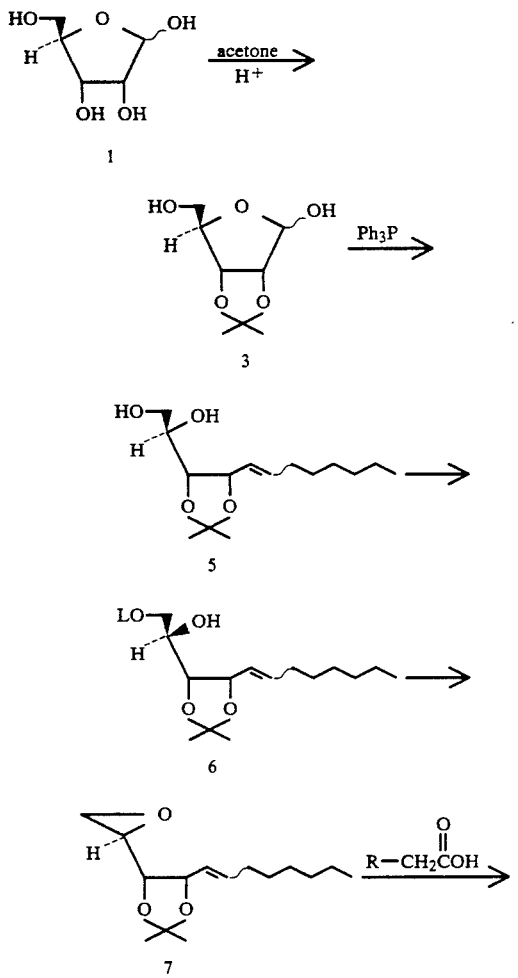

(Abstract continued on next page.)

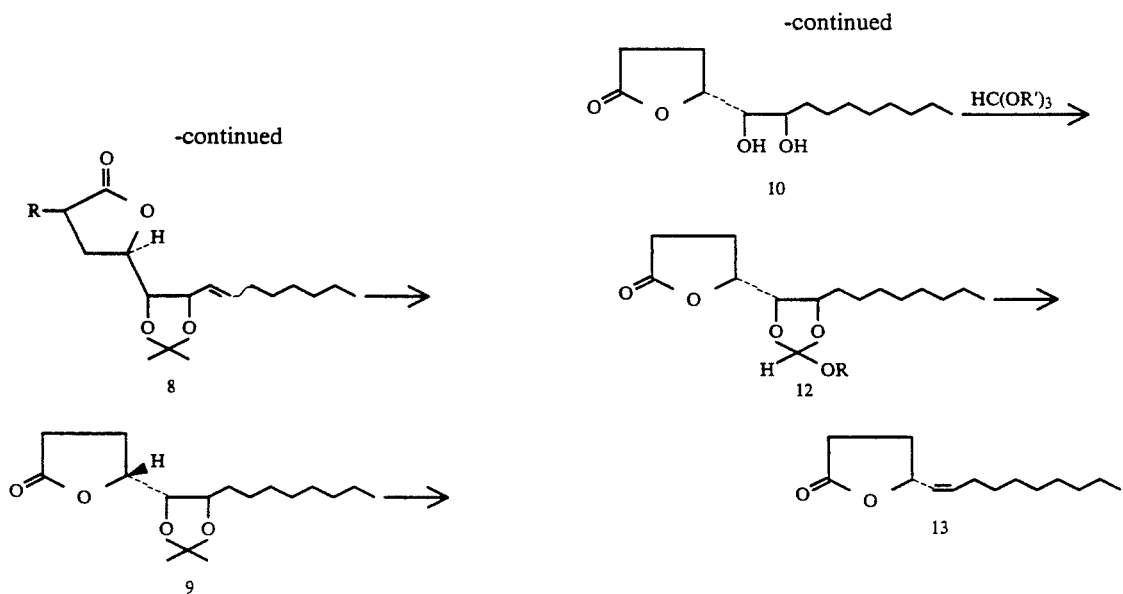
9 Claims, No Drawings

METHOD FOR PRODUCING (R,Z)-5-TETRADECEN-4-OLIDE

BACKGROUND OF THE INVENTION

1. Field of the Invention

This invention relates to a method for producing (R,Z)-5-tetradecen-4-olide. The present substance is a sex pheromone of a Japanese beetle (scientific name: Popillia japonica). This compound is useful for the extermination of the Japanese beetle through a pheromone trap.

2. Description of the Related Art

Japanese beetles are insect pests which live on fruit trees or, for instance grapes, lawn, etc. In recent years, a damaged lawn by Japanese beetles have become a problem especially on a golf course. Moreover, since a large amount of pesticides are used for extermination of Japanese beetles, pesticide pollution has caused a public discussion in the area near to a golf course.

Pheromone traps are able to exterminate a large amount of insect pests by utilizing a small amount of pheromone, and is practically applied for some insects. A pheromone trap against the Japanese beetle is therefore considered to be a useful means in order to solve said problem.

A method described in Agric. Biol. Chem., 51, 635–640 (1987) is known as a method for synthesizing a pheromone of Japanese beetle, i.e., (R,Z)-5-tetradecen-4-olide. This method is performed by synthesizing from arabinose an optically-active intermediate, (4R, 5S, 6R)-5,6-dihydroxytetradecan-4-olide, and then by eliminating diol from said intermediate according to the following steps:

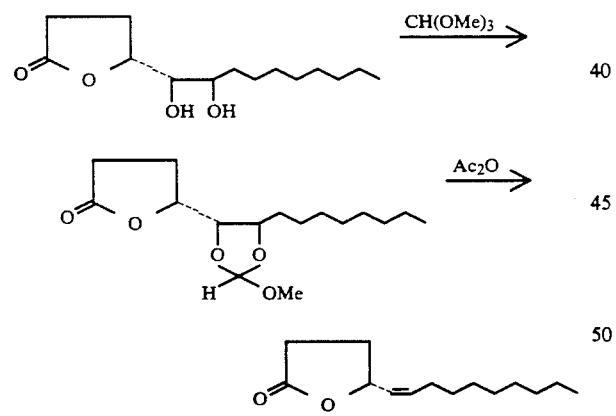

However, this conventional method includes a step for utilizing chromic acid, a harmful reagent, as an oxidizing agent in order to synthesize the optically-active intermediate, (4R,5S,6R)-5,6-dihydroxytetradecan-4-olide. This method thus suffers from problems on practical use in that it lowers safety in synthesis manipulation and it causes environmental pollution through industrial waste.

SUMMARY OF THE INVENTION

The object of the invention is to provide a method for producing a large amount of (R,Z)-5-tetradecen-4-olide by utilizing a few steps, and this method advantageously includes no step of oxidation using chromic acid.

The method for producing (R,Z)-5-tetradecen-4-olide according to the present invention includes the following steps;

a) a step for causing D-ribose 1 to react with acetone 2 to obtain a compound 3, according to the following formula:

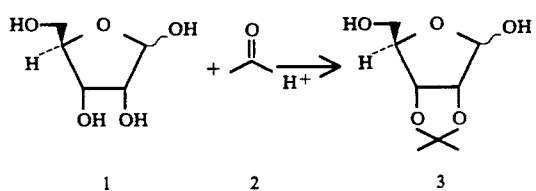

b) a step for causing the compound 3 to react with Wittig reagent 4 to obtain a compound 5, according to the following formula:

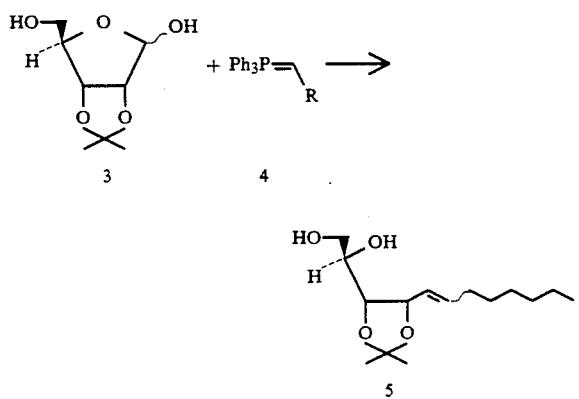

c) a step for selectively converting only a primary hydroxyl group of the compound 5 into a leaving group, —OL, to obtain the following compound 6:

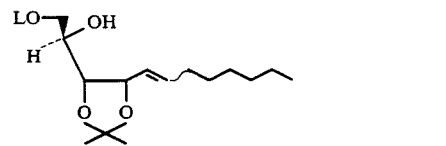

d) a step for treating the compound 6 with a base to obtain the following compound 7:

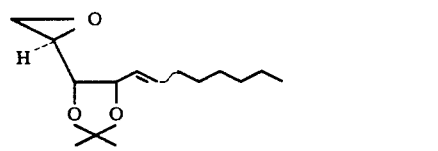

e) a step for causing the compound 7 to react with an acetic acid equivalent in the presence of a base catalyst and then lactonizing the resultant product to obtain a compound 8, according to the following reaction formula:

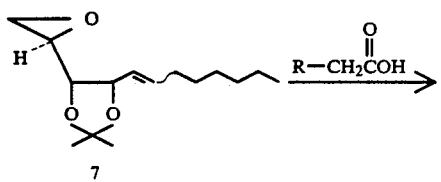

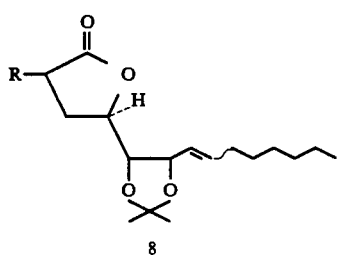

wherein R is an α-substituent of the acetic acid equivalent, f) a step for subjecting the compound 8 to catalytic hydrogenation to obtain the following compound 9:

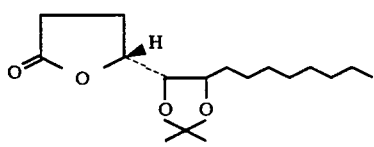

g) a step for hydrolyzing a ketal portion of the compound 9 with acid treatment to obtain the following compound 10:

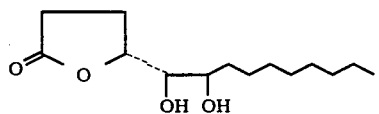

and h) a step for causing the compound 10 to react with orthoformate 11 in order to obtain an orthoester derivative 12, and further eliminating orthoformate from the orthoester derivative 12 through reduction in order to obtain a desired compound 13, according to the following reaction formula:

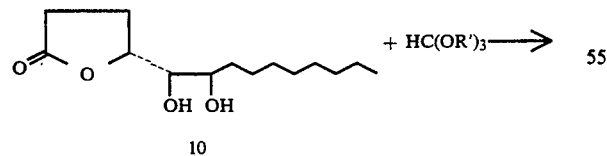

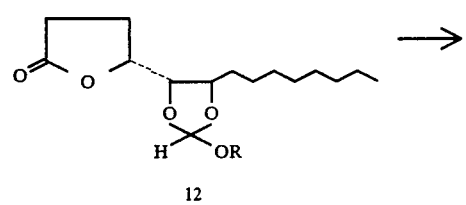

-continued

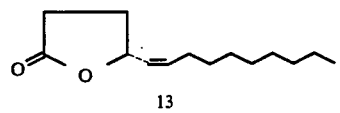

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

DETAILED DESCRIPTION OF THE PREFERRED EMBODIMENTS

D-ribose 1 used for the present invention is easily available in the market at a low cost. Use of D-ribose is therefore one advantage for the present invention.

A step for producing the compound 3 as in the step a) can be also performed according to a known method (J.Biol.Chem., 102, 187–201 (1933)), by protecting 2,3-diol groups of the D-ribose 1 with isopropylidene groups. Namely, the compound 3 is obtained by causing the D-ribose 1 to react with acetone 2 in order to form a ketal.

A step for producing the compound 5 from the compound 3 in the step b) is conducted by well-known Wittig reaction. Specifically, this reaction is performed by cleaving cyclic acetal of the compound 3 and causing the resultant aldehyde to react with Wittig reagent 4, according to the following reaction formulas:

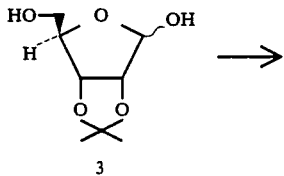

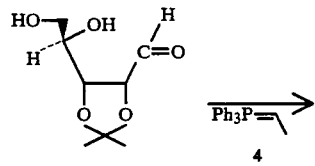

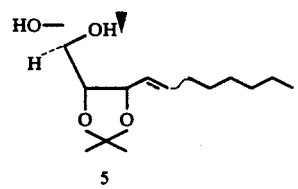

This reaction is also performed by treating 3 to 10 equivalent, preferably 4 to 6 equivalent of phosphonium salt of the following formula with a base such as butyllithium or potassium butoxide at a temperature in the range of −40° C. to 40° C., preferably −10° C. to 10° C., and by further causing the resultant salt to react with the compound 3 at a temperature in the range of −30° C. to 50° C., and preferably, at an ambient temperature:

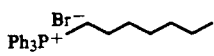

The completion of this reaction requires 1 to 50 hours. A solvent used in the step b) is usually an ether solvent such as tetrahydrofuran and diethylether, but not limited thereto.

A reaction for selectively converting only a primary hydroxyl group into a leaving group —OL in the step c) may be performed according to a general esterification utilizing acid chloride, acid anhydride, etc. For example, a compound 6 whose L is a tosyl group is obtained by causing the compound 5 to react with p-toluenesulfonyl chloride, as in the following formula:

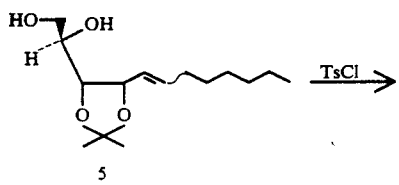

The completion of this reaction requires 1 to 50 hours at room temperature. The L of the compound 6 may also be a methanesulfonyl group or a trifluoromethanesulfonyl group. A solvent utilized in this reaction is pyridine, etc., but not limited thereto.

A reaction for producing a compound 7 by treating the compound 6 with a base in the step d) is a known epoxidation reaction. Examples of a basic compound utilized in this reaction include metal hydroxides such as potassium hydroxide and sodium hydroxide, metal hydrides such as sodium hydride and lithium hydride, and metal alkoxide such as sodium methoxide and potassium butoxide. An amount of the basic compound may be 1 to 7 equivalents, and preferably, 3 to 6 equivalents. Examples of a solvent here includes water, alcohols such as methanol and ethanol, tetrahydrofuran, and a solvent mixture thereof, but not limited thereto. The completion of this reaction requires 1 to 50 hours at room temperature.

An acetic acid equivalent utilized for production of lactone 9 from the compound 7 in the step e) may be acetic acid itself and acetic acid derivatives such as phenylthioacetic acid. The step e) utilizing phenylthioacetic acid is shown as follows:

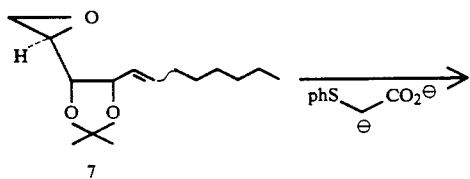

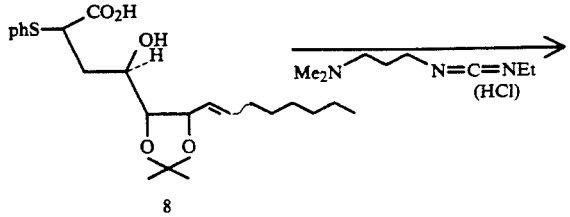

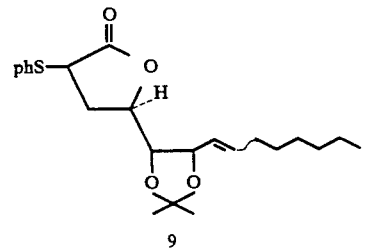

First, one to five equivalents, preferably two to four equivalents of phenylthio acetic acid is treated with a suitable base such as lithium diisopropylamide and lithium hexamethyldisilazide, thereby to generate the dilithio salt of phenylthioacetic acid. This reaction is generally completed in about 1 hour at room temperature. This anion nucleophilically reacts with an epoxy group of the compound 7 in order to cleave an epoxy ring, thus forming a Y-hydroxycarboxylic acid derivative as an intermediate. Next, a suitable lactonizing reagent is added to the intermediate for reaction in order to form a lactone compound 8. The completion of this reaction requires 1 to 50 hours at room temperature. This lactonizing reagent here is not specifically limited, and such a reagent as generally used for lactonization may be used. Examples of these reagents include N-ethyl-N'-(3-dimethylaminopropyl) carbodiimide chloride.

A reaction for producing a compound 9 from the compound 8 in the step f) is performed according to a general catalytic reduction. Specifically, the compound 8 is dissolved into a suitable solvent and stirred under hydrogen atmosphere in the presence of a suitable hydrogenation catalyst such as Raney nickel, platinum, and palladium-carbon. A solvent used here is a alcoholic solvent such as ethanol and methanol, but not limited thereto. The completion of this reaction requires 1 to 50 hours.

In the step g), from the compound 9, isopropylidene group is eliminated which protects diols to obtain a compound 10. This reaction hydrolyzes ketal with an acid catalyst. Examples of the acid catalyst includes mineral acids such as hydrogen chloride and sulphuric acid, organic acids such as trifluoroacetic acid and p-toluenesulphonic acid and acidic ion-exchange resins. A solvent used in this reaction is generally water, dioxane, etc., but not limited thereto. The completion of this reaction requires 0.5 to 10 hours at room temperature.

In the final step h), the objective compound, (R,Z)-5-tetradecen-4-olide 13 is formed from the compound 10. Orthoformate used in this step is not specifically limited, but orthomethylformate and orthoethylformate are preferably utilized. Reductive elimination of orthoester derivative 12 is performed by causing it to react with anhydrous acetic acid. As described in description of the related art, the step h) is already known (Agric.-Biol.Chem., 51, 635-640(1987)). Therefore, this invention is advantageously characterized in the steps a) to g) to obtain the compound 10.

As apparent in the above descriptions, this method of the present invention does not include oxidization through chromic acid in order to form (R,Z)-5-tetradecen-4-olide. Safer operation can thus be obtained in synthesis in comparison with conventional methods, and environmental pollution via industrial waste can be eminently reduced.

Moreover, since D-ribose as the starting material in this invention is available at low cost, and the number of steps required is not larger than that for the conventional methods, the total cost for production can be reduced in this invention.

The present invention will be described in detail by way of the following Example.

EXAMPLE step a)

Synthesis of 2,3-O-isopropylidene-D-ribofuranose (compound 3)

D-ribose 1 of a starting material was reacted with acetone according to the method disclosed in J.Biol.-Chem., 102,187-201 (1933) to form a compound 3. Physical data for the compound 3 were found to be in accord with those in literature.

step b)

Synthesis of (2R, 3R, 4S)-3,4-(isopropylidenedioxy)-5-dodecen-1,2-diol (compound 5)

A suspension was prepared by adding 5.3 g (120 mmol) of heptyltriphenylphosphonium bromide to 315 ml of anhydrous THF. To this suspension, 75 ml (120 mmol) of n-hexane solution containing n-butyllithium (concentration: 1.6 mol/l) was slowly added dropwise. After that, the reaction solution was stirred at 0° C. for one hour. Separately, 4.5 g (24 mmol) of the compound 3 prepared in the step a) was dissolved into 40 ml of anhydrous THF. The resultant solution was slowly added to said reaction solution, followed by stirring at room temperature overnight for reaction.

After the reaction was terminated, the resultant solution was transferred to a saturated sodium chloride solution, followed by extraction with chloroform three times. The obtained organic phase was washed with water, dried over anhydrous magnesium sulfate, and evaporated under vacuum to remove the solvent. The obtained residue was dissolved in diethylether and water, and extracted with diethylether three times. The obtained organic phase was dried over anhydrous magnesium sulfate, and evaporated under vacuum to remove the solvent. The resultant residue was purified by a silica gel column chromatography (eluent; n-hexane: ethyl acetate=2:1) to obtain 5.5 g (20 mmol) of the compound 5. Yield was 85%.

The compound 5 was a mixture of E isomer and Z isomer, and the mixture ratio was E:Z=7:3. $^1$H-NMR data for this product were as follows: $^1$H-NMR (CDCl$_3$):δ, 5.89 (0.7H, dt, J=15.3 & 6.7Hz, E:H-6), 5.77 (0.3H, dt, J=11.0 & 7.1 Hz, Z:H-6), 5.65-5.52 (1H, m, H-5), 5.04 (0.3H, dd, J=9.0 & 6.4 Hz, Z:H-4), 4.67 (0.7H, t, J=7.2Hz, E:H-4), 4.10-4.02 (1H, m, H-3), 3.85-3.65 (3H, m, H-1, H-2), 2,50-2.35 (2H, m, OH), 2.25-2.05 (2H, m, H-7), 1.55-1.25 (14H, m, Me, H-8, H-9, H-10, H-11), 0.88 (3H, t, J=6.7Hz, H-12)

step c)

Synthesis of (2R, 3R, 4S)-2-hydroxy-3,4-(isopropylidenedioxy)-5-dodecenyl-tosylate (compound 6)

To 2 ml of pyridine, 0.20 g (0.73 mmol) of the compound 5 prepared in the step b) was dissolved. To the resultant solution, 0.17 g (0.89 mmol) of p-toluenesulfonyl chloride was added, followed by stirring under anhydrous condition overnight for reaction.

After that, the reaction solution was transferred to a saturated sodium bicarbonate solution, followed by extraction with diethylether three times. The obtained organic phase was dried over anhydrous magnesium sulfate, and evaporated under vacuum to remove the solvent. The residue was dissolved into diethylether, and washed with saturated copper sulfate solution, water, and saturated sodium hydrogen carbonate in this order. The obtained organic phase was dried with anhydrous magnesium sulfate, and evaporated under vacuum to remove the solvent. The obtained residue was purified by utilizing a silica gel column chromatography (eluent; n-hexane: ethyl acetate=5:1) to obtain 0.23 g (0.54 mmol) of the compound 6. Yield was 74%.

$^1$H-NMR data of this product were as follows:
$^1$H-NMR (CDCl$_3$):δ, 7.81 (2H, d, J=8.3 Hz, aromatic-H), 7.35 (2H, d, J=8.3 Hz, aromatic-H), 5.85 (0.7H, dt, J=15.2 & 6.8 Hz, E:H-6), 5.77-5.66 (0.3H, m, Z:H-6), 5.00 (0.3H, ddd, J=9.1 & 5.3 & 0.8 Hz, Z:H-4), 4.64 (0.7H, t, J-6.9 Hz, E:H-4), 4.35-4.27 (1H, m, H-1), 4.15-4.02 (1H, m, H-1), 4.02-3.92 (1H, m, H-3), 3,92-3.84 (1H, m, H-2), 2.45 (3H, s, aromatic-Me), 2.35 (0.3 H, d, J=4.6 Hz, Z:OH), 2.32 (0.7 H, d, J=4.6 Hz, E:OH), 2.15-2.03(2 H, m, H-7), 1.45-1.25 (14 H, m, Me, H-8, H-9, H-10, H-11), 0.88 (3 H, t, J=6.6 Hz, H-12)

step d)

Synthesis of (2R, 3R, 4S)-1,2-epoxy-3,4-(isopropylidenedioxy)-5-dodecene (compound 7)

To 100 ml of anhydrous THF, 2.5 g (6.0 mmol) of the compound 6 prepared in the step c). To the resultant solution, 0.95 g (60% solution, 24 mmol) of sodium hydride was slowly added in argon atmosphere at 0° C. The obtained solution was stirred at room temperature overnight for reaction.

After that, the reaction solution was transferred to saturated ammonium sulfate solution, followed by extraction with diethyether three times. The obtained organic phase was dried with anhydrous magnesium sulfate, and evaporated under vacuum to remove the solvent. The obtained residue was purified by utilizing a silica gel column chromatography (eluent; n-hexane: ethyl acetate=6:1) to obtain 1.4 g (5.3 mmol) of the compound 7. Yield was 88%.

$^1$H-NMR data of this product were as follows:
$^1$H-NMR (CDCl$_3$):δ, 5.91 (0.7 H, dt, J=15.3 & 6.8 Hz, E:H-6), 5.82-5.73 (0.3 H, m, Z:H-6), 5.66-5.53 (1H, m, H-5), 5.06 (0.3 H, ddd, J=8.8 & 6.4 & 0.9 Hz, Z:H-4), 4.70 (0.7 H, t, J=7.2 Hz, E:H-4), 3.75 (1H, t, J=6.7 Hz, H-3), 3.01-2.95 (1H, m, H-2), 2.84-2.79 (1H, m, H-1), 2.71-2.66 (1H, m, H-1), 2.19-2.04 (2 H, m, H-7), 2.15-2.03 (2 H, m, H-7), 1.55-1.23 (14 H, m, Me, H-8, H-9, H-10, H-11), 0.93-0.88 (3H, m, H-12)

step e)

Synthesis of (2RS, 5R, 6S)-5,6-(isopropylidenedioxy)-2-phenylthio-7-tetradecen-4-olide (compound 8)

To 40 ml of anhydrous THF, 2.8 g (17 mmol) of phenylthioacetic acid was dissolved. To the resultant solution, 34 ml (34 mmol) of THF solution (concentration: 1.0 mol/l) containing lithium hexamethyldisilazide was added dropwise. The temperature of the obtained solution was slowly increased to room temperature, and the solution was stirred for one hour, with the temperature maintained at room temperature, for reaction.

Separately, 2.1 g (8.4 mmol) of the compound 7 prepared in the step d) was dissolved in 40 ml of anhydrous THF. The resultant solution was added to the reaction solution prepared as above dropwise, followed by stirring at room temperature overnight for reaction.

After the reaction was terminated, the solution was transferred to 1 mol/l hydrogen chloride solution, followed by extraction with diethylether three times. The obtained organic phase was washed with water twice, with saturated sodium chloride solution once, dried over anhydrous magnesium sulfate, and evaporated under vacuum to remove the solvent.

Next, 5.6 g of the residue was dissolved into 40 ml of anhydrous dichloromethane. To the resultant solution, 2.1 g (11 mmol) of N-ethyl-N'-(3-dimethylaminopropyl)carbodiimide hydrochloride and a catalytic amount of 4-dimethylaminopyridine were added, followed by stirring under anhydrous condition at room temperature for one hour to react.

After that, the reaction solution was transferred to saturated sodium hydrogen carbonate, followed by extraction with dichloromethane three times. The obtained organic phase was dried over anhydrous magnesium sulfate, and evaporated under vacuum to remove the solvent. The obtained residue was purified by utilizing a silica gel column chromatography (eluent; n-hexane: ethyl acetate=8:1) to obtain 2.1 g (5.2 mmol) of the compound 8. Yield was 62%. $^1$H-NMR data for this product were as follows:

$^1$H-NMR (CDCl$_3$):δ, 7.62–7.53 (2 H, m, aromatic-H), 7.44–7.21 (3 H, m, aromatic-H), 5.88–5.77 (0.8 H, m, H-8:E), 5.75–5.64 (0.2 H, m, H-8:Z), 5.47–5.25 (1H, m, H-7), 5.08–4.97 (0.2 H, m, H-6:Z), 4.70–4.63 (0.8 H, m, H-6:E), 4.39–3.88 (3 H, m, H-2, H-4, H-5), 2.75–2.59 (1H, m, H-3), 2.33–2.22 (1H, m, H-3). 2.15–1.98 (2 H, m, H-9), 1.48–1.20 (14 H, m, Me, H-10, H-11, H-12, H-13), 0.92–0.85 (3 H, m, H-14)

step f)

Synthesis of (4R, 5S, 6S)-5,6-(isopropylidenedioxy)-tetradecan-4-olide (compound 9)

0.50 g (1.2 mmol) of the compound 8 prepared in the step e) was dissolved into 15 ml of ethanol. The resultant solution was added with Raney nickel, and heated under reflux in hydrogen atmosphere overnight for reaction.

The reacted solution was filtered through Celite to remove the catalyst, and the obtained filtrate was concentrated under vacuum. The residue was purified by utilizing a silica gel column chromatography (eluent; n-hexane:ethyl acetate=4:1) to obtain 0.27 g (0.90 mmol) of the compound 9. Yield was 73%.

$^1$H-NMR data and IR data for this product were as follows:

$^1$H-NMR (CDCl$_3$):δ, 4.48 (1H, q, J=7, 1Hz, H-4), 4.26–4.11 (1H, m, H-6), 4.02 (1H, dd, J=7.5 & o.0Hz, H-5), 2.67–2.14 (4 H, m, H-2, H-3), 2.30–1.97 (3 H, m, H-3, H-9), 1.70–1.22 (20 H, m, Me, H-7, H-8, H-9, H-10, H-11, H-12, H-13), 0.88 (3 H, t, J=6.7 Hz, H-14)

IR (neat):ν, 2928(s), 2860(s), 1787(s), 1462(m), 1373(m), 1176(w)

step g)

Synthesis of (4R, 5S, 6S)-5,6-dihydroxytetradecan-4-olide (compound 10)

0.96 g (3.2 mmol) of the compound 9 prepared in the step f) was dissolved into 30 ml of 90% trifluoroacetic acid solution. The resultant solution was stirred at room temperature for four hours.

After that, the reaction solution was concentrated under vacuum, and further subjected to azeotropic distillation with toluene to dehydrate. The obtained residue was recrystallized from diethylether to obtain 0.20 g (0.8 mmol) of the compound 10. The filtrate was concentrated under vacuum, and the resultant residue was purified by utilizing a silica gel column chromatography (eluent; n-hexane: ethyl acetate=1:2) to obtain 0.40 g (1.6 mmol) of the compound 10. Total yield was 72%.

Melting point, 1H-NMR data and IR data of this product were as follows:

melting point: 117.0°–119.0° C. (96.0°–97.5° C. in literature)

$^1$H-NMR (CDCl$_3$):δ, 4.47 (1H, dt, J=7.3 & 4.0 Hz, H-4), 3.85 (1H, dd, J=6.0 & 4.0 Hz, H-5), 3.70 (1H, ddd, J=8.8 & 5.9 & 3.0 Hz, H-6), 2.68–2.46 (2 H, m, H-2), 2.44–2.20 (2 H, m, H-3), 2.00–1.65 (2 H, br., OH), 1.62–1.21 (14 H, m, H-7, H-8, H-9, H-10, H-11, H-12, H-13), 0.88 (3 H, t, J=6.7 Hz, H-14)

IR (KBr):ν, 3238(s), 2924(s), 2856(s), 1773(s), 1738(m), 1460(m), 1207(m), 1083(m), 1023(m)

step h)

Synthesis of the objective compound, (R,Z)-5-tetradecen-4-olide (compound 13)

0.10 g (0.39 mmol) of the compound 10 prepared in the step g) was dissolved into 10 ml of dried methylene chloride. To the resultant solution, 100 μl (0.94 mmol) of orthomethylformate and a catalytic amount of p-toluenesulfonic acid were added, followed by stirring in the absence of water at room temperature for thirty minutes.

After that, the reaction solution was chromatographed on a silica gel with diethylether. The obtained eluate was concentrated under vacuum to obtain 0.12 g (0.37 mmol) of a crude product 12. Yield was 95%.

Next, 0.11 g (0.33 mmol) of this compound 12 was dissolved into 4 ml of anhydrous acetic acid. To the resultant solution, a catalytic amount of p-toluenesulfonic acid was added, followed by heating under reflux in the absence of water for 2 hours.

After the reaction was terminated, the solution was cooled, transferred to saturated sodium hydrocarbonate solution, and extracted with chloroform three times. The obtained organic phase was dried over anhydrous magnesium sulfate, and evaporated under vacuum to remove the solvent. The obtained residue was purified by utilizing a silica gel column chromatography (eluent;

n-hexane: ethyl acetate=4:1) to obtain 0.06 g (0.27 mmol) of the compound 13. Yield was 82%.

¹H-NMR data and IR data of this product were as follows:

¹H-NMR (CDCl₃):δ, 5.67 (1H, ddt, J=10,8 & 7.6 & 0.9 Hz, H-6), 5.46 (1H, ddt, J=10.8 & 8.3 & 1.5 Hz, H-5), 5.25 (1H, dddd, J=9.0 & 8.3 & 6.5 & 0.9 Hz, H-4), 2.56 (2 H, m, H-2), 2.38 (1H, ddt, J=12.6 & 12.1 & 6.5 Hz, H-3), 2.11 (2 H, m, H-7), 1.95 (1H, dddd, J=12.6 & 9.1 & 9.0 & 8.2 Hz, H-3), 1.47-1.23 (12 H, m, H-8, H-9, H-10, H-11, H-12, H-13), 0.88 (3 H, t, J=6.7 Hz, H-14)

IR (neat):ν, 930(s), 2858(m), 1781(s), 1462(m), 1180(s), 013(m), 980(m), 909(m)

Additional advantages and modifications will readily occur to those skilled in the art. Therefore, the invention in its broader aspects is not limited to the specific details, and illustrated examples shown and described herein. Accordingly, various modifications may be made without departing from the spirit or scope of the general inventive concept as defined by the appended claims and their equivalents.

What is claimed is:

1. A method for producing (R,Z)-5-tetradecen-4-olide represented by the following formula:

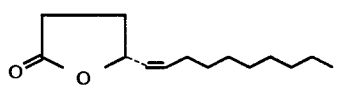

13 which comprises
a) reacting D-ribose 1 with acetone 2 to obtain compound 3, according to the following reaction scheme:

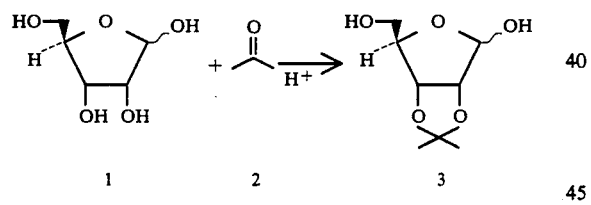

b) reacting compound 3 with Wittig reagent 4 to obtain compound 5, according to the following reaction scheme:

HO—⟨O⟩—OH
H       + Ph₃P=⟨R⟩ →
O  O
 X 3         4

HO—⟨OH⟩
H
O  O
 X

5 wherein R in reagent 4 is a linear saturated hydrocarbon group having 7 carbon atoms, c) selectively converting only a primary hydroxyl group of the compound 5 into a leaving group, —OL, to obtain the following compound 6:

LO—⟨OH⟩
H
O  O
 X

6 d) treating compound 6 with a base to obtain the following compound 7:

▽—O
H
O  O
 X

7 e) reacting compound 7 with an acetic acid equivalent in the presence of a base catalyst and then lactonizing the resultant product to obtain a compound 8, according to the following reaction scheme:

▽—O                    O
H            R—CH₂COH
O  O         ⟶
 X

7

R—⟨O⟩
   O
   H
O  O
 X

8 wherein R is an α-substituent of the acetic acid equivalent, f) subjecting compound 8 to catalytic hydrogenation to obtain the following compound 9:

O⟨O⟩—H
O  O
 X

9 g) hydrolyzing a ketal portion of the compound 9 by an acid treatment to obtain the following compound 10:

O⟨O⟩
OH OH

10 and h) reacting compound 10 with orthoformate 11 to obtain an orthoester derivative 12, and further eliminating orthoformate from the orthoester derivative 12 through reduction to obtain a desired compound 13, according to the following reaction scheme:

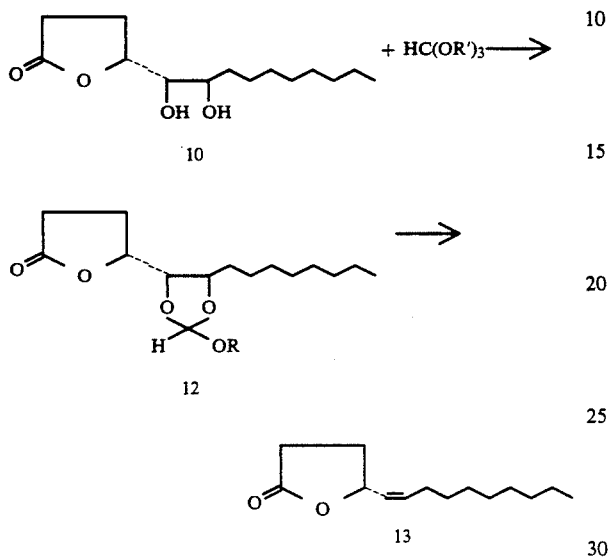

wherein R' in compound 11 is methyl or ethyl.

2. A method for producing (R,Z)-5-tetradecen-4-olide represented by the following formula:

consisting of:

a) reacting D-ribose 1 with acetone 2 to obtain compound 3, according to the following reaction scheme:

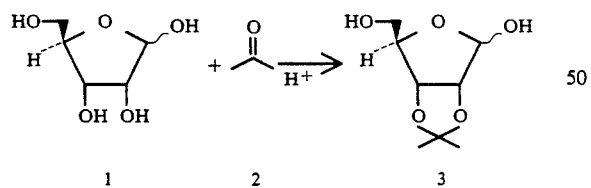

b) reacting compound 3 with Wittig reagent 4 to obtain compound 5, according to the following reaction scheme:

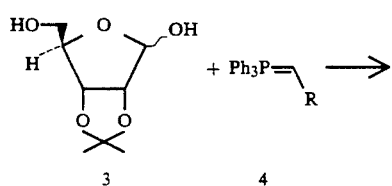

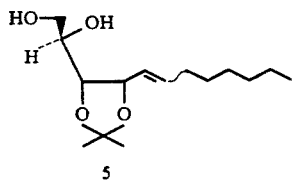

wherein R in reagent 4 is a linear saturated hydrocarbon group having 7 carbon atoms, c) selectively converting only a primary hydroxyl group of the compound 5 into a leaving group, —OH , to obtain the following compound 6:

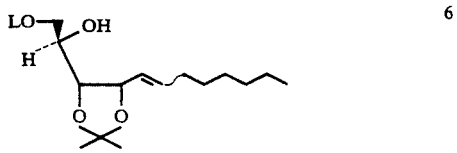

d) treating compound 6 with a base to obtain the following compound 7:

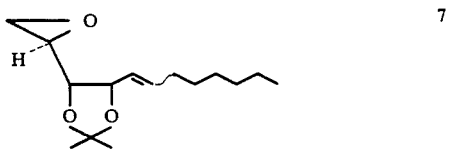

e) reacting compound 7 with an acetic acid equivalent in the presence of a base catalyst and then lactonizing the resultant product to obtain a compound 8, according to the following reaction scheme:

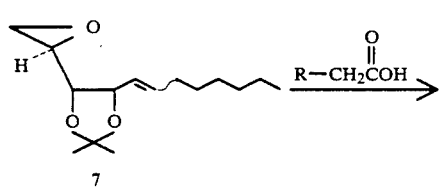

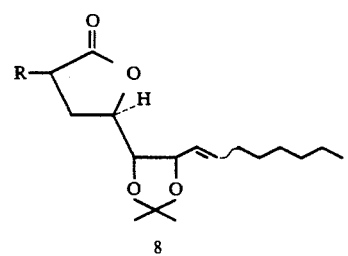

wherein R is an α-substituent of the acetic acid equivalent, f) subjecting compound 8 to catalytic hydrogenation to obtain the following compound 9:

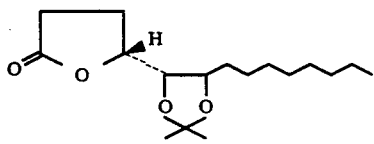

g) hydrolyzing a ketal portion of the compound 9 by an acid treatment to obtain the following compound 10:

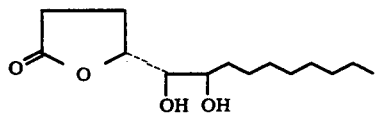

and h) reacting compound 10 with orthoformate 11 to obtain an orthoester derivative 12, and further eliminating orthoformate from the orthoester derivative 12 through reduction to obtain a desired compound 13, according to the following reaction scheme:

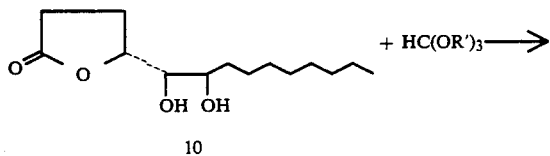

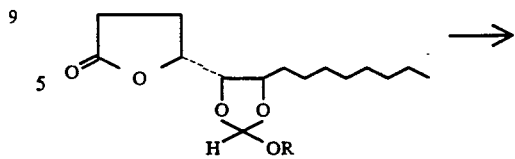

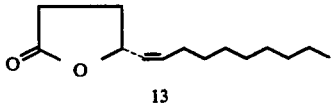

wherein R' in compound 11 is methyl or ethyl.

3. The method of claim 1, wherein L is a tosyl group.

4. The method of claim 1, wherein L is a methanesulfonyl group, a trifluoromethane sulfonyl group or a trifluoromethanesulfonyl group.

5. The method of claim 1, wherein L is a methanesulfonyl group or a tosyl group.

6. The method of claim 1, wherein the base is selected from the group consisting of metal hydroxides, metal hydrides and metal alkoxide.

7. The method of claim 1, wherein the base is present in an amount of 1 to 7 equivalents.

8. The method of claim 1, wherein a reagent for lactonizing is N-ethyl-N'-(3-dimethylaminopropyl) carbodiimide chloride.

9. The method of claim 1, wherein the acid treatment is with a mineral acid, an organic acid or an acidic ion-exchange resin.

* * * * *